(12) United States Patent
Thomes et al.

(10) Patent No.: US 9,750,685 B2
(45) Date of Patent: Sep. 5, 2017

(54) OPHTHALMIC DEVICE HAVING THERAPEUTIC AGENT DELIVERY CAPABILITY AND METHOD OF FORMING SAME

(71) Applicant: Novartis AG, Basel (CH)

(72) Inventors: Brett E. Thomes, Fort Worth, TX (US); Stephen J. Van Noy, Fort Worth, TX (US); Chi-Chun Tsai, Fort Worth, TX (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/958,097

(22) Filed: Dec. 3, 2015

(65) Prior Publication Data
US 2016/0081921 A1 Mar. 24, 2016

Related U.S. Application Data (63) Continuation of application No. 12/505,558, filed on Jul. 20, 2009, now Pat. No. 9,233,069.

(60) Provisional application No. 61/082,352, filed on Jul. 21, 2008.

(51) Int. Cl.
*A61K 31/165* (2006.01)
*A61K 31/4985* (2006.01)
*A61K 9/00* (2006.01)
*A61K 47/32* (2006.01)

(52) U.S. Cl.
CPC .......... *A61K 9/0051* (2013.01); *A61K 31/165* (2013.01); *A61K 31/4985* (2013.01); *A61K 47/32* (2013.01)

(58) Field of Classification Search
CPC .................. A61K 31/619; A61K 31/4985
See application file for complete search history.

(56) References Cited

U.S. PATENT DOCUMENTS

| | | |
|---|---|---|
| 4,240,163 A | 12/1980 | Galin |
| 5,098,443 A | 3/1992 | Parel et al. |
| 5,290,892 A | 3/1994 | Namdaran et al. |
| 5,403,901 A | 4/1995 | Namdaran et al. |
| 5,470,932 A | 11/1995 | Jinkerson |
| 5,554,187 A | 9/1996 | Rizzo, III |
| 5,693,095 A | 12/1997 | Freeman et al. |
| 5,843,186 A | 12/1998 | Christ |
| 6,010,391 A | 1/2000 | Lewellen et al. |
| 6,106,554 A | 8/2000 | Bretton |
| 6,238,799 B1 | 5/2001 | Opolski |
| 6,353,069 B1 | 3/2002 | Freeman et al. |
| 6,713,080 B1 | 3/2004 | Aiache et al. |
| 6,866,936 B2 | 3/2005 | Opolski |
| 7,090,888 B2 | 8/2006 | Snyder et al. |
| 8,071,648 B2 | 12/2011 | Wong |
| 2001/0001836 A1 | 5/2001 | Cumming |
| 2004/0013655 A1 | 1/2004 | Shiozawa et al. |
| 2004/0202625 A1 | 10/2004 | Daniloff et al. |
| 2006/0122277 A1 | 6/2006 | Wong |
| 2007/0218104 A1 | 9/2007 | Kunzler et al. |

FOREIGN PATENT DOCUMENTS

| | | |
|---|---|---|
| EP | 0774983 | 12/2002 |
| JP | 2001-505792 | 5/2001 |
| JP | 2001-316426 | 11/2001 |
| JP | 2008-521926 | 6/2008 |
| RU | 2251394 C2 | 5/2005 |
| WO | WO 98/25652 | 6/1998 |
| WO | 2004/016259 | 2/2004 |
| WO | WO 2006/060618 | 6/2006 |
| WO | 2006/126095 | 11/2006 |
| WO | 2008/073193 | 6/2008 |

OTHER PUBLICATIONS

European Examination Report corresponding to EP application 09790618.4 dated Nov. 12, 2012, 6 pages.
González-Aramundiz et al., 2012, "Polypeptides and Polyaminoacids in Drug Delivery", Expert Opin. Drug Deliv., 92, 183-201.
OSN SuperSite, "Cataract surgery Antibiotic-soaked IOLs show efficacy against bacteria" by Michela Cimberle, http://www.osnsupersite.com Jun. 3, 2008.
PCT International Search Report for corresponding PCT/US2009/051103 with Feb. 4, 2011 mailing date, 5 pages.
PCT International Written Opinion for corresponding PCT/US2009/051103 with Feb. 4, 2011 mailing date, 4 pages.
Römpp Chemie Lexikon, 1995, 3 pages.

*Primary Examiner* — Zohreh Fay
(74) *Attorney, Agent, or Firm* — Patrick M. Ryan (57) ABSTRACT

The present invention is directed to ophthalmic devices that are loaded with therapeutic agent. The devices provide prolonged release of the therapeutic agent to the eye. The ophthalmic devices are typically formed of an ophthalmic material that is particularly desirable for the loading of therapeutic agent and/or the therapeutic agent is typically particularly desirable for loading to the ophthalmic material.

24 Claims, 6 Drawing Sheets

OPHTHALMIC DEVICE HAVING THERAPEUTIC AGENT DELIVERY CAPABILITY AND METHOD OF FORMING SAME

CROSS-REFERENCE TO RELATED APPLICATION

The present application is a continuation of U.S. application Ser. No. 12/505,558 filed Jul. 20, 2009 (now allowed), which claims priority to U.S. Provisional Patent Application No. 61/082,352, filed Jul. 21, 2008, the entire contents of which are incorporated herein by reference.

TECHNICAL FIELD OF THE INVENTION

The present invention is related to an ophthalmic device that is loaded with a therapeutic agent. More particularly, the present invention is related to an ophthalmic device (e.g., an intraocular lens (IOL)) that is loaded with therapeutic agent (e.g., anti-inflammatory agent, antiproliferative agent, immunosuppressive agent or any combination thereof) such that the device can provide delivery of the therapeutic agent to the eye for an extended period of time after the device has been applied to the eye.

BACKGROUND OF THE INVENTION

In recent years, the number of ophthalmic surgeries such as cataract surgeries where an intraocular lens (IOL) is delivered internally within an eye of an individual has steadily increased. IOLs have been developed and inserted into various locations of the eye and can be used to supplement or correct the vision provided by the natural crystalline lens of the eye or can replace the natural crystalline lens of the eye. Lenses that supplement or correct the vision without replacing the natural crystalline lens are typically referred to as Phakic Lenses while lenses that replace the natural crystalline lens are typically referred to as Aphakic lenses. Phakic lenses can be located within the anterior chamber (AC) of the eye (AC Phakic lenses) or the posterior chamber (PC) of the eye (PC Phakic Lenses).

While IOLs have provided millions of individuals with improved eyesight, IOLs can also exhibit drawbacks. In particular, IOLs can be a cause of ophthalmic maladies such as secondary cataracts or posterior capsule opacification (PCO).

To assist in avoiding PCO, therapeutic agents such as anti-inflammatories or anti-proliferatives can be administered to an eye after insertion of an IOL therein. These therapeutic agents are typically delivered via topical delivery methods such as ointments or ophthalmic drops. Such methods, however, have at least two significant drawbacks. First, it can be difficult for these topically delivered therapeutic agents to reach target locations within the eye since portions of the eye can act as significant physiologic barriers that inhibit the penetration of the therapeutic agents into the back of the eye. Second, the efficacy of these topical delivery methods is typically dependent upon an individual's compliance with a prescribed regimen for application of the ointment or drops to the eye.

In view of these drawbacks, it would be highly desirable to provide an ophthalmic device that is inserted within the eye and that delivers desired amounts of a therapeutic agent over a period of time after cataract surgery. Such a device could be used to deliver agents that assist in avoiding PCO. Moreover, insertion of such a device within the eye, after surgery or at another time, could additionally or alternatively be used to deliver therapeutic agents that inhibit other ophthalmic diseases or maladies such as glaucoma, macular edema, retinopathy, macular degeneration, chronic inflammation, infection or the like.

To effectively develop such a device, there needs to be a mechanism by which the therapeutic agent is continuously or periodically released from the device over the desired period of time. However, for extend release time periods, control over the release of the therapeutic agents can be extremely difficult. Advantageously, a relationship has been discovered between particular ophthalmic materials and release of therapeutic agents from those materials and that relationship can be exploited to provide for desired release periods.

SUMMARY OF THE INVENTION

The present invention is directed to an ophthalmic device that is at least partially formed of an ophthalmic material. The ophthalmic material is typically acrylic, hydrophobic or both. The ophthalmic device is typically loaded with a therapeutic agent. In preferred embodiments of the invention, the therapeutic agent and the ophthalmic material are hydrophobic for assisting in loading the material with the agent and for assisting in prolonging the release of the therapeutic agent from the ophthalmic material.

The ophthalmic device may be suitable for location within an eye or location upon an outer surface of the eye. In a preferred embodiment, the ophthalmic device, which will be partially or entirely formed of the ophthalmic material, is an IOL or a device suitable for location within the eye along with an IOL.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION OF THE INVENTION

The present invention is predicated upon the provision of an ophthalmic device that is at least partially formed of an ophthalmic material that is suitable for location upon but more preferably within an eye of an individual. The device may also be located at or within or locations of the human body, however, the device is particularly desirable for ophthalmic applications.

The ophthalmic material of the device is suitable for loading with therapeutic agent that is to be delivered to the eye. The ophthalmic material can also be suitable for use as an intraocular lens (IOL) although, as is discussed further below, the material may be provide as an IOL or in another configuration. The material or one or more components of the material are typically relatively hydrophobic and, preferably, the therapeutic agent also exhibits a degree hydrophobicity. In one preferred embodiment, the material is provided as an Aphakic IOL and the therapeutic agent includes a substantial amount of anti-inflammatory agent for reducing inflammation that may be present after cataract surgery.

The ophthalmic material is preferably a polymeric material that is comprised of a hydrophobic component, a hydrophilic component or both. The ophthalmic material is also typically acrylic, which, as used herein, means that that the material includes as least one acrylate. The ophthalmic material can also include other ingredients as explained further below.

The hydrophobic component can be comprised of a single monomer or multiple different monomers and those monomers can form polymers, which may be homopolymers or copolymers. Each of the monomers included in the hydrophobic component will be hydrophobic or will provide hydrophobicity to the ophthalmic material once formed. Preferably, a substantial portion (e.g., at least 60, 80 or 95% by weight or the entirety) of the hydrophobic component is formed of acrylate. Suitable monomers for the hydrophobic component include, but are not limited to: 2-ethylphenoxy methacrylate; 2-ethylphenoxy acrylate; 2-ethylthiophenyl methacrylate; 2-ethylthiophenyl acrylate; 2-ethylaminophenyl methacrylate; 2-ethylaminophenyl acrylate; phenyl methacrylate; phenyl acrylate; benzyl methacrylate; benzyl acrylate; 2-phenylethyl methacrylate; 2-phenylethyl acrylate; 3-phenylpropyl methacrylate; 3-phenylpropyl acrylate; 4-phenylbutyl methacrylate; 4-phenylbutyl acrylate; 4-methylphenyl methacrylate; 4-methylphenyl acrylate; 4-methylbenzyl methacrylate; 4-methylbenzyl acrylate; 2-2-methylphenylethyl methacrylate; 2-2-methylphenylethyl acrylate; 2-3-methylphenylethyl methacrylate; 2-3-methylphenylethyl acrylate; 24-methylphenylethyl methacrylate; 2-4-methylphenylethyl acrylate; 2-(4-propylphenyl)ethyl methacrylate; 2-(4-propylphenyl)ethyl acrylate; 2-(4-(1-methylethyl)phenyl)ethyl methacrylate; 2-(4-(1-methylethyl)phenyl)ethyl acrylate; 2-(4-methoxyphenyl)ethyl methacrylate; 2-(4-methoxyphenyl)ethyl acrylate; 2-(4-cyclohexylphenyl)ethyl methacrylate; 2-(4-cyclohexylphenyl)ethyl acrylate; 2-(2-chlorophenyl)ethyl methacrylate; 2-(2-chlorophenyl)ethyl acrylate; 2-(3-chlorophenyl)ethyl methacrylate; 2-(3-chlorophenyl)ethyl acrylate; 2-(4-chlorophenyl)ethyl methacrylate; 2-(4-chlorophenyl)ethyl acrylate; 2-(4-bromophenyl)ethyl methacrylate; 2-(4-bromophenyl)ethyl acrylate; 2-(3-phenylphenyl)ethyl methacrylate; 2-(3-phenylphenyl)ethyl acrylate; 2-(4-phenylphenyl)ethyl methacrylate; 2-(4-phenylphenyl)ethyl acrylate; 2-(4-benzylphenyl)ethyl methacrylate; 2-(4-benzylphenyl)ethyl acrylate; combinations thereof or the like. In preferred embodiments, the hydrophobic component includes or is substantially entirely formed of (i.e., at least 90% by weight) one or more monomers that are phenyl acrylates or methacrylates, particularly those selected from the group consisting of 2-phenyl ethyl acrylate (PEA), 2-phenyl ethyl methacrylate (PEMA).

The hydrophobicity of the hydrophobic component can typically be measured according to the Sessile Drop Technique. To measure the hydrophobicity, the ingredients of the hydrophobic component, and only the hydrophobic component, can be cured in accordance with the curing protocol for the ophthalmic device to form a solid flat substrate. Of course, for such curing, the amount of curing agent, if needed, can be adjusted. In particular, the hydrophobic component will typically represent a percentage of the overall curable material in the ophthalmic device and the amount of curing agent can be adjusted to be the same percentage of overall curing agent that forms the ophthalmic device. Then, according to the Sessile Drop Technique, a drop of water is placed (or allowed to fall from a certain distance) surface of the substrate. When the liquid has settled, its contact angle is measured with a goniometer. For purposes of the present invention, ingredients, particularly monomers, that assist in making this contact angle greater than 50° are considered part of the hydrophobic component and it is preferably that the contact angle measured in this manner be greater than 50°, more typically greater than 55° and even possibly greater than 60°.

The hydrophilic component, when included, can be comprised of a single monomer or multiple different monomers and those monomers can form polymers, which may be homopolymers or copolymers. Each of the monomers of the hydrophilic component must be hydrophilic or provide hydrophilicity to the ophthalmic material once formed. Like the hydrophobic component, it is preferable for a substantial portion (e.g., at least 60, 80 or 95% by weight or the entirety) of the hydrophilic component to be formed of acrylate. Suitable monomers for the hydrophilic component include, but are not limited to: 2-hydroxyethylmethacrylate; 2-hydroxyethylacrylate; N-vinylpyrrolidone; glyceryl methacrylate; glyceryl acrylate; polyethylene oxide mono- and dimethacrylates; and polyethylene oxide mono- and diacrylates. In preferred embodiments, the hydrophilic component includes or is substantially entirely formed of (i.e., at least 90% by weight) one or more monomers that are hydroxyalkyl acrylates or methacrylates such as hydroxyethyl methacrylate (HEMA).

The hydrophilicity of hydrophilic component can be measured in the same manner that is described for the hydrophobic component. For purposes of the present invention, ingredients, particularly monomers, that assist in pushing the contact angle for the hydrophillic to below 40° are considered part of the hydrophobic component and it is preferable that the contact angle measured in this manner be less than 40°, more typically less than 35 and even possibly less than 30°.

The ophthalmic device of the present invention can additionally include a variety of further ingredients, which may or may not be part of the hydrophobic or hydrophilic ingredients as further described below. Such ingredients can include, without limitation, flexibilizers, UV absorbers, polymerization agents, curing and/or cross-linking agents, combinations thereof or the like.

It is contemplated that multiple different compounds can be employed as polymerization, curing and/or cross-linking agents for polymerizing and cross-linking the ophthalmic device as needed to form a polymer matrix. As examples, peroxides such as benzophenone peroxide or peroxycarbonate (e.g., bis-(4-t-butulcyclohexyl)peroxydicarbonate) or azonitrile such as azobisisobytyronitrile, and the like may be used to initiate polymerization and/or cross-link the hydrophobic component, the hydrophilic component or both. Suitable cross-linking agents can also include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and the like. Preferred cross-linking agents are ethylene glycol dimethacrylate (EGDMA) and 1,4-butanediol diacrylate (BDDA). In general, the amount of any polymerization initiator, cross-linking agent or both utilized will be about 10% (w/w) or less of the ophthalmic material of the present invention.

Any ultraviolet absorbing material included in the ophthalmic material will typically be a compound which absorbs ultraviolet light (i.e., light having a wavelength shorter than about 400 nm), but does not absorb a substantial amount of visible light. The ultraviolet absorbing compound can be incorporated into a monomer mixture and entrapped in a polymer matrix when the monomer mixture is polymerized. Suitable ultraviolet absorbing compounds include substituted benzophenones, such as 2-hydroxybenzophenone, and 2-(2-hydroxyphenyl)benzotriazoles and tin compounds such as O-methyl tinuvin P. The UV abosorber may become entrapped in the polymer matrix by a physical entrapment only or may also be reacted into the matrix.

In addition to ultraviolet absorbing materials, ophthalmic devices made of the ophthalmic material of the present invention may include colored dyes, such as the yellow dyes disclosed in U.S. Pat. No. 5,470,932, which incorporated herein by reference for all purposes.

The ophthalmic device is typically formed through polymerization and/or cross-linking. In particular, the ingredients of the ophthalmic material are combined and the polymer forming components, particularly the hydrophobic component, the hydrophilic component or both, are polymerized and preferably cross-linked to form a polymer matrix. Preferably, although not necessarily required, heat is employed during the polymerization and/or cross-linking process. While it is generally contemplated that the ophthalmic material of the present invention may be a thermoplastic, it is generally preferred that such material is thermoset.

The additional ingredients may or may not be part of the hydrophobic component or the hydrophilic component of the ophthalmic material. For clarity, these ingredients, particularly the ultraviolet absorbers as well as the polymerization and/or cross-linking agents are only to be considered as part of the hydrophobic or hydrophilic components if they become reacted (i.e., chemically reacted) into a polymer matrix with these components and they exhibit the requisite hydrophobic or hydrophilic characteristic upon formation of the ophthalmic device. Thus, for example, a 1,4 butanediol diacrylate cross-linking agent would be considered as part of the hydrophobic component since it would typically be reacted into a polymer matrix and it exhibits the requisite hydrophobic characteristic. In contrast, a tin UV absorber that is merely physically entrapped by (not reacted into) the polymer matrix would not be considered part or either the hydrophobic or hydrophilic components.

Figure 8:
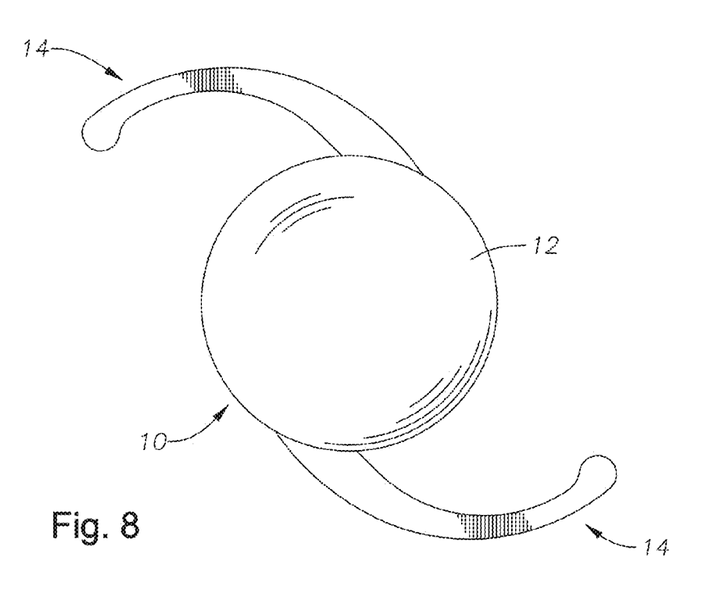
FIG. 8 is a depiction of an exemplary ophthalmic device in accordance with an aspect of the present invention.
Figure 9:
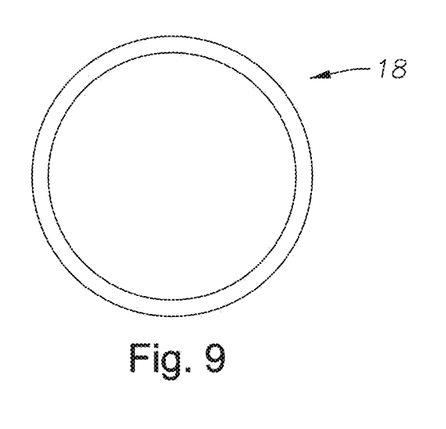
FIG. 9 is a depiction of another exemplary ophthalmic device in accordance with an aspect of the present invention.

At some point prior to and/or during the polymerization and cross-linking, the ophthalmic material is typically located within a mold for shaping of the material into the ophthalmic device. Generally, it is contemplated that the ophthalmic material could be shaped in any desired configuration that is suitable for topical location upon the eye or intravitreal location or intravitreal depot injection within the eye. The ophthalmic device and/or ophthalmic material can be located partially within the eye (e.g., as a plug) or substantially entirely within the eye (e.g., as a intraocular lens or lens associated component). In a most preferred embodiment, the ophthalmic material is shaped into an IOL which one or more convex surfaces and refractive index suitable for assisting or providing vision to a human eye. The IOL could be AC Phakic, PC Phakic or Aphakic. It also is contemplated that the device could be shaped as a haptic of an IOL. For illustrative purposes, FIG. 8 shows an intraocular lens assembly 10 having an intraocular lens 12 and haptics 14, either or both of which could be the ophthalmic device formed of the ophthalmic material of the present invention. It is contemplated that the ophthalmic device of the present invention could be a portion of an IOL or haptic or could be a mass (e.g., a disc) of material separate from an IOL, which could be inserted in the eye with or without an IOL. Again for illustrative purposes, FIG. 9 shows a disc in 18 the shape of a ring which could be located in an eye with an IOL.

Figure 10:
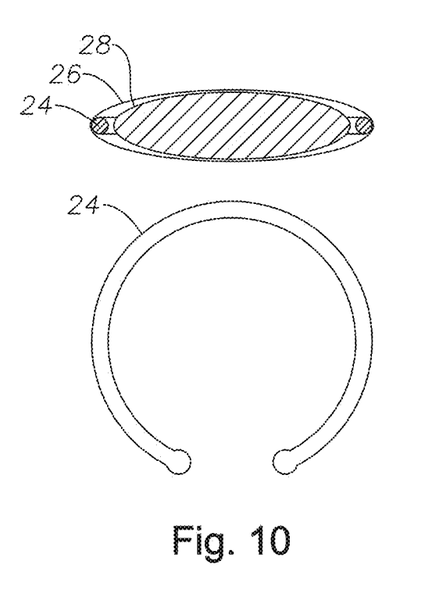
FIG. 10 is a depiction of another exemplary ophthalmic device in accordance with an aspect of the present invention.

In one preferred embodiment, which is illustrated in FIG. 10, the ophthalmic material can be shape as a capsular tension ring 24. In such embodiment, the tension ring 24 is located within the capsular bag 26 of an eye for maintaining tension upon and/or space within the capsular bag 26. Such a ring 24 can substantially encircle an IOL 28 that has been located within the capsular bag 26 and, advantageously, will typically avoid being an obstruction to vision through the IOL 28.

It will be understood that it may be possible for the ophthalmic material of the present invention to biodegradable or non-biodegradable within the eye. However, it is generally preferable that the ophthalmic material be part of a structure that has longevity within the eye and is, therefore, typically non-biodegradable within the eye.

Once the ophthalmic device is formed, therapeutic agent is associated with the ophthalmic device such that upon application of the device to the eye, it can provide for release of the therapeutic agent over an extended time period. Advantageously, it has been found that the hydrophobic component of the present invention, particularly when that component is acrylic, provides an affinity for hydrophobic therapeutic agents where the agents tend to dissociate from the hydrophobic component in an aqueous environment at a rate that is substantially slower than the agents dissociate from other materials. As such, the hydrophobic component can be used to deliver the therapeutic agents to an eye or other aqueous environment over an extended period of time.

Hydrophobic therapeutic agents are defined herein as being any agent that is sparingly soluble in aqueous media (e.g., not completely dissolved in the media at the concentration at which it is administered in an aqueous composition) particularly when immersed in such aqueous media without agents to assist in solubilizing the agent. Generally is contemplated that the therapeutic agent may include one or multiple agents. A preferred class of therapeutic agents includes ophthalmic drugs, particularly hydrophobic and/or low solubility ophthalmic drugs. Non-limiting examples include: anti-glaucoma agents, anti-angiogenesis agents; anti-infective agents; anti-inflammatory agents; anti-proliferative agents; growth factors and growth factor inhibitors; immunosuppressant agents; and anti-allergic agents. Antiglaucoma agents include beta-blockers, such as timolol, betaxolol, levobetaxolol, and carteolol; miotics, such as pilocarpine; carbonic anhydrase inhibitors, such as brinzolamide and dorzolamide; prostaglandins, such as travoprost, bimatoprost, and latanoprost; seretonergics; muscarinics; dopaminergic agonists; and adrenergic agonists, such as apraclonidine and brimonidine. Anti-angiogenesis agents include anecortave acetate (RETAANE™, Alcon™ Laboratories, Inc. of Fort Worth, Tex.) and receptor tyrosine kinase inhibitors. Anti-infective agents include quinolones, such as ciprofloxacin, moxifloxacin, and gatifloxacin, and aminoglycosides, such as tobramycin and gentamicin. Antiinflammatory agents include non-steroidal and steroidal anti-inflammatory agents, such as suprofen, diclofenac, bromfenac, ketorolac, nepafenac, rimexolone, and tetrahydrocortisol. Anti-proliferative agents includes, without limitation, colchcine, mitomycine-C, methotrexate, daynomycin, daunorubicin and 5-fluorouracil. Growth factors include, without limitation, epidermal growth factor (EGF), fibroblast growth factor (FGF), hepatocyte growth factor (HGF), nerve growth factor (NGF), platelet-derived growth factor (PDGF) and transforming growth factor beta (TGF-β). Immunosuppressant agents include, without limitation, calcineurin inhibitors (e.g., cyclosporine) and mammalian target of rapamycin (MTOR) inhibitors (e.g., sirolimus, zatarolimus, everolimus, temsirolimus); Anti-allergic agents include olopatadine and epinastine. The ophthalmic drug may be present in the form of a pharmaceutically acceptable salt, such as timolol maleate, brimonidine tartrate or sodium diclofenac. As will be understood by the skilled artisan, non-steroidal anti-inflammatory agents (NSAIDs) such as nepafenac are particularly desirable for assistance in prevention of secondary cataracts.

The therapeutic agent can be applied to the ophthalmic material and/or device in particle or other form. If the therapeutic agent or a portion thereof is in particle form, it may, in one embodiment, be desirable to grind or otherwise machine the particles to a very small size. It may even be desirable to machine the particles into submicron or even nano-particles.

It is generally preferred that the therapeutic agent exhibit a degree of hydrophobicity such that the therapeutic agent has a relatively high partition coefficient log P (PC Log P) as can be determined in accordance with Sangster, James (1997) Octanol-Water Partition Coefficients, Fundamentals and Physical Chemistry, vol. 2 of Wiley Series in Solution Chemistry, Chichester, John Wiley & Son Ltd. [ISBN 978-0471973973]. Typically, the therapeutic agent will have a PC Log P that is at least 1.0, more typically at least 1.6, even more typically at least 2.0 and even possibly at least 2.5. For therapeutic agent comprised of two or more hydrophobic agents, it is preferred that both of the agents have a PC Log P greater than these values.

Multiple different protocols may be employed for applying the therapeutic agent to the ophthalmic device. It is generally contemplated that the therapeutic agent may be reacted to form a bond with the ophthalmic material of the ophthalmic device, Alternatively or additionally, the therapeutic agent may be associated with the ophthalmic material by other forces tending to maintain the therapeutic agent in contact with or directly adjacent the ophthalmic material. Without being bound by theory, it is believed that these forces are hydrophobic interaction, van der Waals forces, physical entrapment, hydrogen bonding forces, electric charge forces or any combination thereof.

In one preferred embodiment, the therapeutic agent is dissolved in solvent such as acetone, methanol, benzene, toluene, alcohol, a combination thereof or the like to form a therapeutic agent solution. The ophthalmic material, the ophthalmic device or both are submerged and soaked in the solution for a period of time. Thereafter, the ophthalmic material, the ophthalmic device or both are removed from solution and dried, for example, under heat and/or vacuum conditions such that an amount of therapeutic agent is disposed upon the ophthalmic material. The agent, once applied to the device will typically be disposed over outwardly facing peripheral surfaces formed of the ophthalmic material although the agent may be disposed over internal surfaces as well.

The amount of therapeutic agent disposed upon the ophthalmic material can vary widely depending upon the therapeutic agent itself and the desired dosing of the agent. Generally, the total weight of therapeutic agent disposed upon the ophthalmic material is at least about 0.01 microgram and is typically less than about 1 milligram. In a highly preferred embodiment wherein the therapeutic agent is entirely or substantially entirely an NSAID such as nepafenac, the ophthalmic device is an IOL (e.g., an Aphakic IOL) or a ring to be placed in the capsular bag (e.g., a capsular tension ring), the amount of therapeutic agent is typically at least about 5 nanogram and more typically at least about 10 microgram and is typically less than about 10 milligrams and more typically less than about 500 micrograms.

While the hydrophobic component of the ophthalmic material tends to attract the hydrophobic therapeutic agent, the hydrophilic component, when included, does not provide the same attraction. As such, it has been found that the inclusion of a hydrophilic component tends to accelerate the release of the therapeutic agent by the ophthalmic material and/or device. Thus, in a preferred embodiment, the ophthalmic device or material can include a balance of hydrophobic and hydrophilic acrylate to achieve a desired output or release profile of the therapeutic agent. By inclusion of greater amounts of the hydrophilic component, the release of therapeutic agent can be accelerated.

The rate of release of therapeutic agent can vary widely depending upon the therapeutic agent employed and the properties of the ophthalmic material. Moreover, the rate of release of therapeutic agent can, at least to some degree, vary depending upon the individual to whom the ophthalmic device is applied. However, a consistent measure of release rate can be developed by immersing the ophthalmic device in a Balanced Salt Solution (BSS) and measuring the release at various time intervals. Specifics for such a measurement are discussed in the examples and comparative data below. For the present invention, BSS is a sterile physiological balanced salt solution of Sodium Chloride (NaCl), Potassium Chloride (KCl), Calcium Chloride ($CaCl_2.H_2O$), Magnesium Chloride ($MgCl_2.6H_2O$), Sodium Acetate ($C_2H_3NaO_2.3H_2O$), and Sodium Citrate Dihydrate ($C_6H_5Na_3O_7.2H_2O$). BSS is isotonic to the tissues of the eyes. Each milliliter contains the following: Sodium Chloride 0.64%, Potassium Chloride 0.075%, Calcium Chloride 0.048%, Magnesium Chloride 0.03%, Sodium Acetate 0.39%, Sodium Citrate 0.17%, Sodium Hydroxide and/or Hydrochloric Acid (to adjust pH), and the remainder is Water.

Generally, for the present invention, it is desirable for less than 80% or even less than 50% by weight of the therapeutic agent to be released from the ophthalmic device in BSS over a period that is at least three days, more typically at least one week, still more typically at least two weeks, possibly at least 30 days and even possibly at least 90 or 180 days and it is desirable for greater than 50% or even greater than 80% by weight of the therapeutic agent to be released in BSS over a time period that is less than 730 days, more typically less than 365 days, still more typically less than 180 days and even possibly less than 90 days. In a preferred embodiment where the therapeutic agent is entirely or substantially entirely (i.e., at least 90% by weight) a non-steroidal anti-inflammatory drug such as nepafenac, it is desirable for less than 80% or even less than 50% by weight of the therapeutic agent to be released in BSS over a time period that is at least 2 days, more typically at least one week and still more typically at least 10 days and it is desirable for greater than 50% or even greater than 80% by weight of the therapeutic agent to be released in BSS over a time period that is less than 180 days, more typically less than 45 days, still more typically less than 25 days and even possibly less than 15 days.

In addition to, or as an alternative to utilizing the attraction between the ophthalmic material and the therapeutic agent, coatings can be employed to assist in loading the therapeutic agent to the ophthalmic device. Such coatings can increase or decrease the loading of the therapeutic agent to a particular ophthalmic material and/or increase or decrease the rate of release of the therapeutic agent from the ophthalmic material. Such coatings can also be used to apply a therapeutic agent to an ophthalmic device where there is little or no attraction between the ophthalmic material that forms the device and the therapeutic agent.

In one embodiment, the therapeutic agent is mixed in a coating and the coating is then applied to (e.g., dip coated onto) the ophthalmic material and/or device. In an alternative embodiment, the coating is applied to (e.g., dip coated onto) the ophthalmic material and/or device and then the therapeutic agent can be applied directly onto the coating using the solvent/therapeutic agent techniques described above or other techniques.

The coating can be formed of a variety of materials, but preferably includes one or more polymers. In one embodiment, the coating is an aqueous based coating that includes one or more polymers that are typically biocompatible. Preferably, the one or more polymers can form a matrix that entraps the therapeutic agent only to release the agent over a period of time one applied with the ophthalmic device to the eye. Such a matrix can be formed by heating the coating and/or the ophthalmic device to which the coating has been applied. Examples of potentially suitable coatings are disclosed in U.S. Pat. Nos. 6,238,799 and 6,866,936, both of which are incorporated herein by reference for all purposes. One suitable coating is sold under the tradename LubrilAST and is commercially available from AST (Advanced Surface Technology) Products, Inc., 9 Linnell Circle, Billerica, Mass., 01821. In one embodiment, the use of a coating with a polymer matrix can provides a way of delivering hydrophilic drugs (e.g., Diclofenac Sodium: log P=1.1, Colchicine: log P=1.3 and Mitomycine C: log P=0.44) from a hydrophobic intraocular implant (e.g., acrylic IOL or ring).

It is also contemplated that prolonged release of therapeutic agent from the ophthalmic device can be achieved by direct loading of drug encapsulated nanoshperes, microspheres or liposome where the encapsulations are made of acrylate or other hydrophobic polymers. Additionally or alternatively, therapeutic agent can be pre-processed to form substantially uniform size/shape of nano- or micro-size particles, which will then be loaded into the ophthalmic device to provide a controlled long term therapeutic agent release.

It is even further contemplated that laser or other energy can be focused on the ophthalmic material in order to heat the material to change release kinetics and/or open additional porosity for therapeutic agent release by the ophthalmic device. Still further, it is contemplated that, in the process of making the ophthalmic device, appropriate process conditions can be applied to form micro- or nano-pockets or vacuoles inside the material of the device. The pockets or vacuoles can then function as additional reservoirs for increasing drug load. The size and density of micro- or nano-pockets/vacuoles can be controlled so they would not impact optical performances of the implant.

Advantageously, the ophthalmic device of the present invention can, whether used with a coating or without a coating, provide quite desirable release profiles for therapeutic agent being release over a period of times. Moreover, particularly when the ophthalmic devices are located within the eye (e.g., as an IOL or capsular tension ring), the ophthalmic devices of the present invention can very efficiently provide therapeutic agents to the intraocular regions of the eye. Further, it has been found that loading the therapeutic agent loaded ophthalmic devices of the present invention exhibit very little, if any, loss in optical and/or mechanical performance.

EXAMPLES AND COMPARATIVE DATA

Single-piece hydrophobic soft acrylic IOLs were formed of 65% of 2-phenylethyl acrylate (PEA), 30% of 2-phenylethyl methacrylate (PEMA), 3.2% of 1,4 butanediol diacrylate (BDDA), and 1.8% O-methyl tinuvin P (OMTP, UV absorber) and were named A1 IOLs. Single-piece hydrophobic soft acrylic IOLs were formed of 80% of PEA, 15% of hydroxyethyl methacrylate (HEMA), 3.2% of BDDA and 1.8% OMTP and were named A2 IOLs. The equivalent water contents at 37° C. were determined to be 0.25% and 1.4% for A1 and A2 IOLs, respectively. Discs with 6 mm diameter and 1 mm thickness were also made according to the above formulations and they are similarly named A1 and A2 discs. Surface area of discs is 75.36 mm$^2$. A 9 mm size intraocular ring implant formed of A1 material was also fabricated and it was named A1 intraocular implant. Surface area of ring implant is 121.62 mm$^2$.

Example 1

Figure 1:
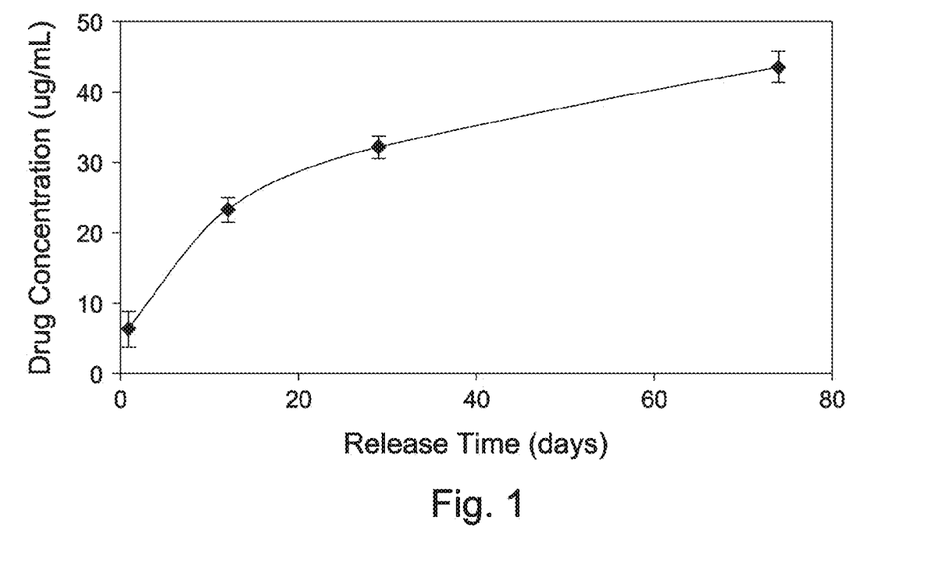
FIG. 1 is a graph of exemplary drug release over time for an ophthalmic device in accordance with an aspect of the present invention.

A 10 mg/mL of Nepafenac drug solution was made in a 5:1 acetone/methanol solution. The A1 IOL was immersed in the drug solution for 48 hrs at room temperature (RT~23° C.) for drug uptake. Drug loaded IOL was then removed from the drug solution, rinsed with blank methanol solvent to wash-off surface drugs, followed by vacuum dry at 50° C. for 4 hrs to remove residual solvents. For drug release study, each drug loaded IOL was placed individually in 0.5 mL of BSS and incubated at 37° C. Total amount of drug release at 1, 12, 30 and 75 days was assayed by high performance liquid chromotography (HPLC) and the results are graphically shown in FIG. 1.

Example 2

A 10.23 mg/mL of nepafenac was made in a 5:1 acetone/methanol solution. The A1 intraocular implant was immersed in the solution for 48 hrs at RT for drug uptake.

Figure 2:
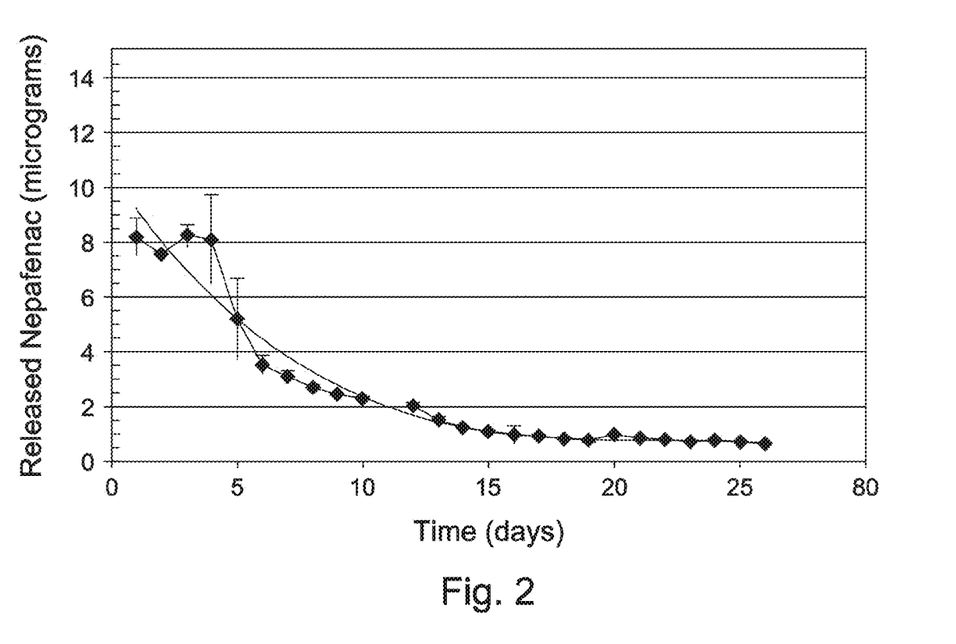
FIG. 2 is another graph of exemplary drug release over time for an ophthalmic device in accordance with an aspect of the present invention.

Drug loaded disc was then removed from the solution, rinsed clean with 5:1 acetone/methanol solution (no drug) to wash-off surface drugs, followed by vacuum dry at 50° C. for 4 hrs to remove residual solvents. For drug release study, each drug loaded disc was placed individually in 0.5 mL of BSS and incubated at 37° C. The BSS was replaced daily for 26 days. Daily released of drug was assayed by HPLC and the results are graphically shown in FIG. 2.

Example 3

Figure 3:
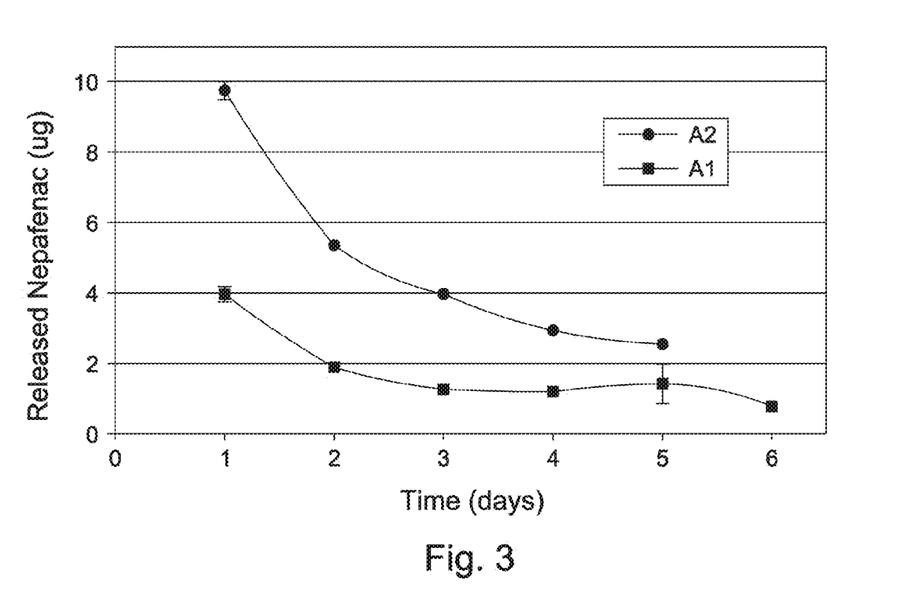
FIG. 3 is another graph of exemplary drug release over time for an ophthalmic device in accordance with an aspect of the present invention.

A 10.23 mg/mL of nepafenac was made in a 5:1 acetone/methanol solution. A1 discs and A2 discs were immersed in the solution for 48 hrs at RT for drug uptake. Drug loaded disc was then removed from the solution, rinsed clean in a 5:1 acetone/methanol solution (no drug) to wash-off surface drugs, followed by vacuum dry at 50° C. for 4 hrs to remove residual solvents. For drug release study, each drug loaded disc was placed individually in 0.5 mL of BSS and incubate at 37° C. The BSS was replaced daily for a week. Daily release of drug from A1 and A2 discs was assayed by HPLC and the results are graphically shown in FIG. 3.

Example 4

Figure 4:
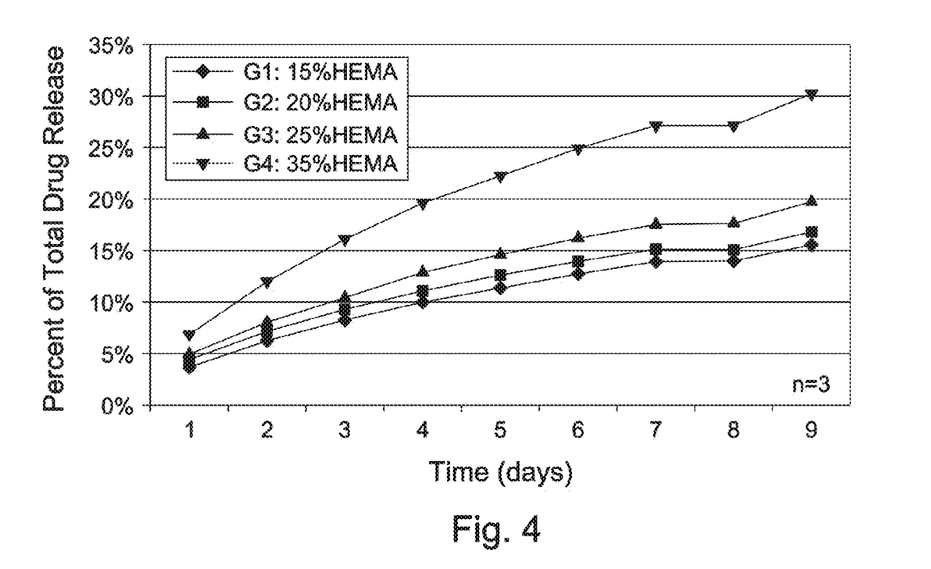
FIG. 4 is a graph of exemplary drug release over time for multiple ophthalmic devices in accordance with an aspect of the present invention.

To evaluate other acrylic IOLs with respect to therapeutic agent uptake and release, the PEA and HEMA ratio was varied in the A2 formulation to obtain acrylic co-polymer discs with wide spectra of material properties from soft more hydrophobic to more rigid, hydrophilic IOL materials, the details of which are shown in Table A below. The uptake study was done by soaking disc samples in a 2.5 mg/mL of nepafenac in 5:1 acetone/methanol solution for 48 hrs at RT, followed by cleaning with 1:1 acetone/methanol mixture (no drug) to remove surface drug. Drug release study was done by incubating sample individually in 0.5 mL of BSS at 37° C. The BSS was replaced daily for 10 days. Daily released of drug was assayed by HPLC and the results are shown graphically in FIG. 4.

TABLE A

| Group Name | Formulation Composition | Qty of Drug Loading (ug) |
| --- | --- | --- |
| G1 | 80% PEA/15% HEMA | 52.52 |
| G2 | 75% PEA/20% HEMA | 52.10 |
| G3 | 70% PEA/25% HEMA | 49.60 |
| G4 | 60% PEA/35% HEMA | 35.28 |

As can be seen, more hydrophobic acrylate materials result in higher drug uptake than more hydrophilic acrylate material but result in slower drug release of the material.

Example 5

Figure 5:
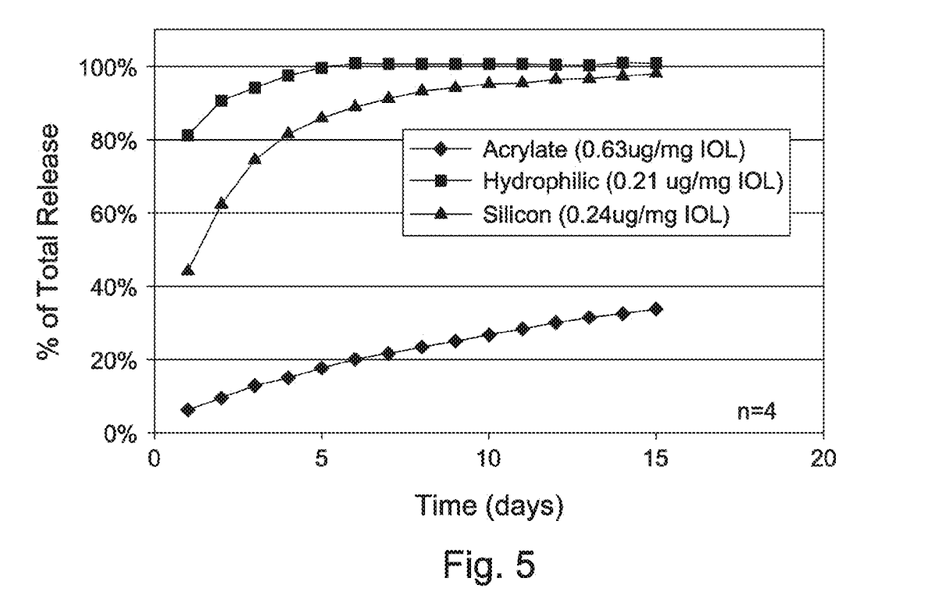
FIG. 5 is another graph of exemplary drug release over time for multiple ophthalmic devices in accordance with an aspect of the present invention.

To compare drug loading and releasing from different IOL and contact lens, a study was carried out using commercially available lenses including an Acrylic IOL, a Silicone IOL, and a hydrophilic Contact Lens. The solution constituents were tethered in order to maximize the drug loading capacity of each lens material. Nevertheless, the drug solution concentration and loading time were the same regardless of the lens materials. The drug loading conditions is shown in Table B below. Drug release study was performed for up to 2 weeks and the results are shown in FIG. 5.

TABLE A2

| Group | Nepafenac Solution | Soak Time | Rinse Method |
| --- | --- | --- | --- |
| Acrylic (A) | 0.5 mg/mL 5:1 Acetone:Methanol | 4 hrs | Methanol rinse |
| Silicone (S) | 0.5 mg/mL 5:1 THF:Methanol | 4 hrs | Methanol rinse |
| Contact Lens (C) | 0.5 mg/mL 5:1 H20:Methanol | 4 hrs | Methanol rinse |

As can be seen, drug loading capacity in silicone IOL and hydrogel contact lens were significantly less than those in the acrylic IOL. In addition, loaded drug was released quickly from silicone and hydrogel lens within the first few days. In contrast, the acrylic lens was able to hold more drugs and release them gradually for an extended period of time.

Example 6

Figure 6:
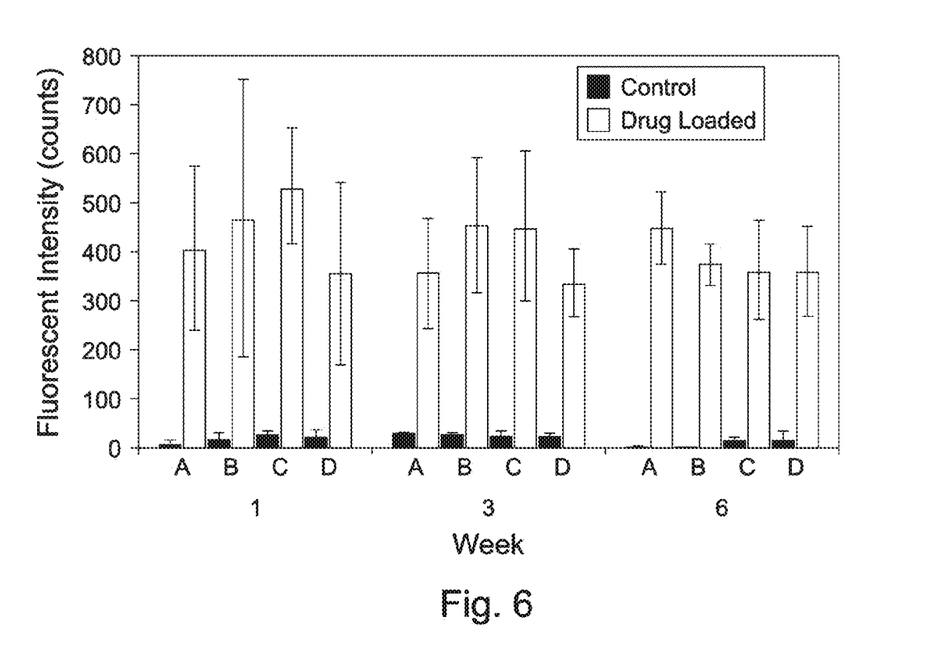
FIG. 6 is a graph of fluorescent intensity over time as an indication of drug release in accordance with an aspect of the present invention.

A1 IOLs were loaded with drug by immersing the IOLs in 5 mg/mL of curcumin drug in acetone for 12 hours. After surface cleaning with Acetone and BSS, the IOLs were implanted as Aphakic IOLs in one of two eyes of New Zealand White rabbit. Prior to implant, the rabbits' natural lens was removed by following the standard phacoemulsification cataract removal procedure. The $2^{nd}$ eye without any implant served as a control. The rabbits were sacrificed at different time periods and the eyes removed. Fluorescence light emission from curcumin drug molecule in each sample eye was imaged by Confocal Laser Scanning Microscopy (CLSM) to obtain a high resolution drug distribution image. The results are shown graphically in FIG. 6 and specifically shown for Regions A and C (lateral sclera regions) of the eyes, Region B (the cornea and anterior chamber regions) of the eyes and Region D (the fovea and macular regions) of the eyes.

Example 7

Figure 7:
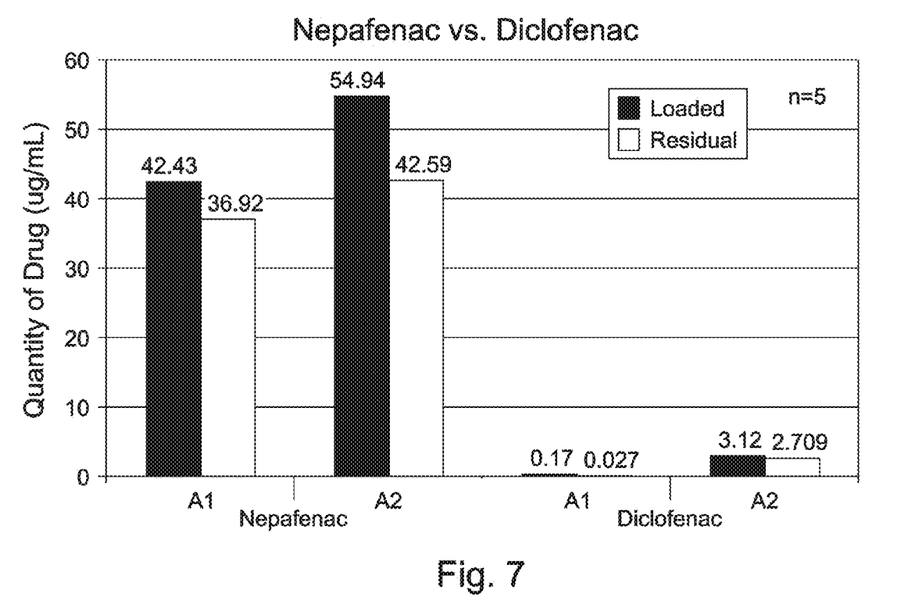
FIG. 7 is a comparative graph of drug release of different drugs in accordance with an aspect of the present invention.

Both 2.5 mg/mL of nepafenac (PC log P=2.1) and 2.5 mg/mL of diclofenac sodium (PC log P=1.1) solution were made. A1 and A2 discs were soaked for drug update in each solution for 4 hours. Daily drug release study in BSS was conducted for 2 weeks. The amount of drug loading and release are illustrated in FIG. 7. As can be seen, a more hydrophobic A1 material loads more drugs, both nepafenac and diclofenac sodium, than a less hydrophobic A2 material. Both materials pick up high amount of hydrophobic nepafenac drugs but only limited less hydrophobic diclofenac sodium drug.

Through experimentation with different concentrations of drug in solution and different amounts of soaking time in those solutions, it was found that the amount of therapeutic agent loaded to the ophthalmic devices could be changed. However, the hydrophobicity of the ophthalmic material and/or the hydrophobicity of the therapeutic agent were typically the overriding factors that determined ability to load amounts of agent to the devices.

Example 8

IOLs were coated with LubrilAST coating/drug solution. Diclofenac was mixed directly with coating solution and the IOLs were dip coated in the coating/drug solution. The coating formulation was modified such that the concentrations of PVP in the coating/drug solution were 20%, 14%, 5%, and 2% by weight. Diclofenac concentration was held constant at 31 mg/mL Lenses were dip coated with a single layer of coating and dried in a 65° C. oven for 4 hours. Lenses were tested in BSS in the same manner as described previously and measured using the spectrophotometer.

Figure 11:
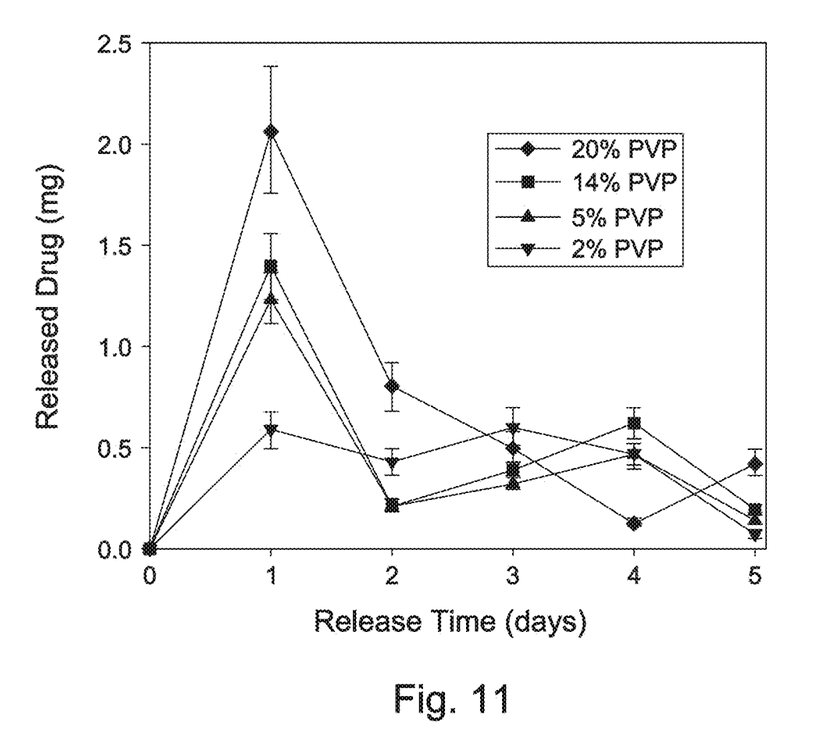
FIGS. 11 and 12 are graphs of exemplary drug release over time for coated ophthalmic devices in accordance with an aspect of the present invention
Figure 12:
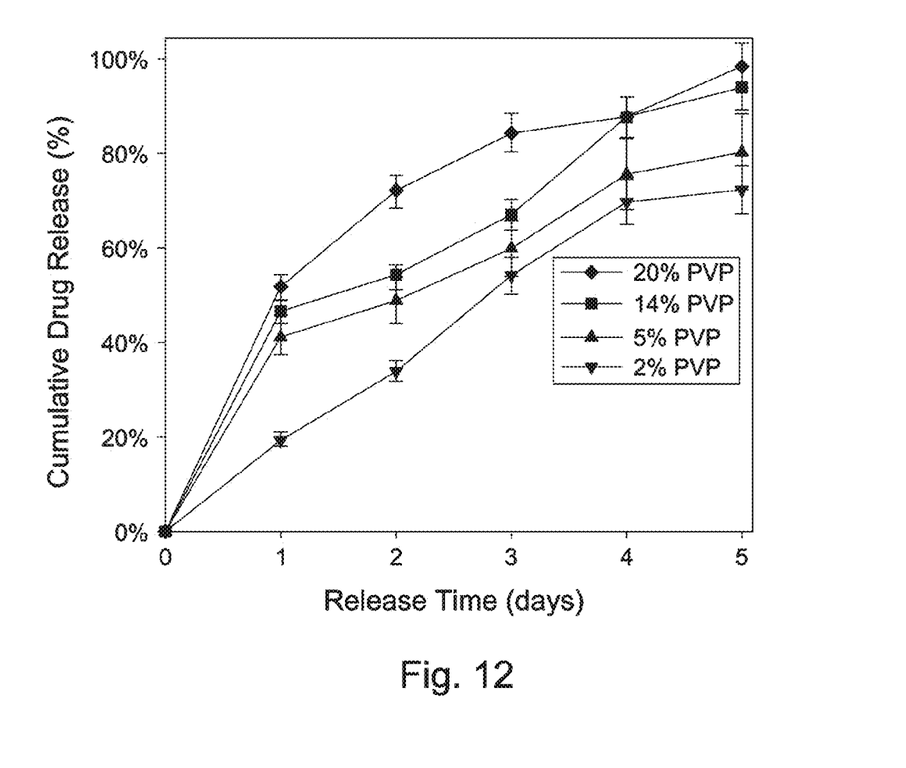

It was found that the drug release rates decreased as the PVP content decreased as can be seen in FIG. 11. With 20% PVP content, 98.2% of the drug was released after 5 days on average (n=3). However, with 2% PVP only 71.9% of the total drug was released after 5 days on average (n=3) (FIG. C2). Moreover, the amount of diclofenac released on a daily basis was significantly affected by the PVP content. As can be seen in FIG. 12, Coating with 2% of PVP released diclofenac at a steady rate for 4 days while other concentrations decreased significantly after 1 day release. Thus Reduction of PVP content significantly prolongs the duration of drug released over 5 days.

Example 9

Diclofenac coating solutions were varied in order to determine the release rates for various drug concentrations incorporated into the coating. The range of concentrations included 5.2, 14.9, 42.8, and 80.1 mg/mL of diclofenac to coating solution. The calculated total drug loading for each concentration is 0.5453, 1.636, 4.699 and 8.795 mg, respectively. Diclofenac is soluble in water up to 50 mg/mL One concentration was chosen outside this range in order to determine the effects of concentrations of stability of the coating and effects on release rates. The others dissolved easily into the coating solution while the high concentrations did not as indicated by the presence of undissolved crystals in the coating solution. The crosslinker content was 1.5% for all coatings. Lenses were coated with 7 layers of each coating. Coating thicknesses were not significantly different as indicated by dry weight measurements of the coated lens.

Lenses were tested in BSS in the same manner as described previously and measured using the spectrophotometer. The release rates for each of the coatings for the first 3 days were significantly different. From day 4 to day 10 drug release rates leveled off and remained nearly consistent throughout this time period. Drug levels near the end of the 10 day period for the other concentrations also fell below the limit of detection of the proposed test method.

Example 10

Release rates for colchicine were obtained for coatings with a range of concentrations, including 2.6, 10.5, 30.3, and 61.2 mg/mL The quantity of drug contained within the coating for each lens was calculated based on the weight gain of the lens after coating and known shrinkage and weight changes of coating after drying. Lenses coated with 2.6 mg/mL drug-coating solution contained approximately 0.0316 mg of colchicine. Lenses coated with 10.5 mg/mL drug-coating solution contained approximately 0.116 mg of colchicine. Lenses coated with 30.3 mg/mL drug-coating solution contained approximately 0.336 mg of colchicine. Lenses coated with 61.2 mg/mL drug-coating solution contained approximately 0.694 mg of colchicine. Based on in vitro studies, the target concentration for colchicine is 0.0005 mg/mL based on results that showed LEC migration and proliferation was inhibited at concentrations as low as 0.0005 mg/mL The limit of detection for colchicine using this analytical technique was 0.0083 mg/mL Drug concentrations were obtained on each sample for 8 days. However, after 8 days all concentrations fell below the limit of detection. At this time, the test solution was replaced and lenses were allowed to soak for an additional 18 days (28 total days) in order to obtain measurable drug concentrations. In vitro drug release data indicates that lenses coated with 2.6 mg/mL coating solution released these quantities for 8 days and then falls below the limit of detection. Lenses coated with 10.5 mg/mL coating solution, as well as the higher concentration coating solutions, released quantities above 0.0083 mg/mL for at least 8 days. Colchicine release was detected after 28 days in BSS at 37° C. (n=3) for coatings loaded with varying drug concentration levels.

Example 11

The quantity of drug contained within the coating for each lens was calculated per previously described methods. Lenses coated with 2 mg/mL drug-coating solution contained approximately 0.138 mg of Mitomycin-C (MMC). Based on in vitro studies, the target concentration for MMC is 0.0005 mg/mL based on results that showed LEC migration and proliferation was inhibited at concentrations as low as 0.0005 mg/mL The limit of detection for MMC using this analytical technique was 0.010 mg/mL After 11 days, MMC continued to be released from the coating at levels above the limit of detection. After the initial 2 days of drug release, drug release rates do not vary significantly. Approximately 20% of the total MMC loaded into the lens remains after 11 days of soaking in BSS at 37° C. MMC is released from the coating up to 11 days after hydrating in BSS at 37° C. (n=3) Levels after 11 days are below the detection limit for MMC for this method.

Example 12

Acrylate lenses (ACRYSOFT® II lenses) were loaded separately with six different therapeutic agents: ascorbic acid, aspirin, colchicine, nepafenac, ketorolac and lidocaine. Release of each of the therapeutic agents from the lenses was determined over a period of 7 days using HPLC. The released drug concentrations were measured using A Waters 2695 Separations Module with a Waters 2699 PDA detector and a Symmetry® C18 column (4.6×75 mm) Calibration curves were constructed for each drug using various concentrations (10, 50, 100, 500, 1000 µg/ml).

The lenses were loaded using a therapeutic agent solution made of acetone and therapeutic agent at a concentration of 3 mg/ml. The lenses soaked in this solution for 90 minutes. The solutions were poured out over a grid-mesh to retrieve the lenses and the lenses were air dried overnight in a closed chamber. On the following day, the lenses were soaked in an acetone:methanol (1:1) solution for 5 minutes and vortexed lightly. The lenses were then removed and allowed to air dry for about 2 hours. The lens was then vacuumed dried at 50° C. overnight. Therapeutic agent loaded lenses (1 lens for each drug) were placed in an Eppendorf tube to which 0.5 ml HPLC grade water was added. The disk was incubated at 37° C., 5% $CO_2$ and release medium was replaced every 24 hours over a period of 7 days. The amount of drug in the release media was analyzed using HPLC.

Various conditions were tried and the HPLC method was optimized for each therapeutic agent.

Nepafenac was tested according to HPLC methods as substantially described above.

For ascorbic acid, the mobile phase included distilled water and 2 mM 1-Octane sulfonic acid sodium salt, methanol, and glacial acetic acid [55:44.5:0.5 (v/v)]. Standards were made in the mobile phase. The injection volume was 25 µl and flow rate 0.5 ml/min. The detection wavelength was fixed at 263 nm.

For aspirin, the mobile phase included methanol, glacial acetic acid, distilled water [30:2:68 (v/v)]. Standards were made in water and the injection volume was 25 µl. The sample flow rate was maintained at 1 ml/min and the detection was carried out at 254 nm.

For colchicine, the mobile phase included acetonitrile and 3% Acetic acid [60:40 (v/v)] and the standards were made in mobile phase. The HPLC flow rate was maintained at 1 ml/min with an injection volume of 25 μl. The detection was carried out at 245 nm.

For ketorolac, the mobile phase included acetonitrile, and 0.2% v/v glacial acetic acid [40:60 (v/v)]. The standards were made in methanol and injection volume was 20 μl. The flow rate was maintained at 1 ml/min with the detection wavelength set at 313 nm.

For lidocaine, the mobile phase included a mixture of 350 ml methanol, 150 ml distilled water, 10 ml Glacial acetic acid and 1.6 g sodium dodecyl sulfate. The mobile phase was filtered through a 0.22 μm filter. Lidocaine standards were made in the mobile phase. The injection volume was set at 25 μl and flow rate at 1 ml/min. The detection was carried out at 250 nm.

Total release of therapeutic agent from the lenses after 7 days is summarized in Table 1 below.

TABLE I

|  | 7 days release (μg) | MW | M.P. (° C.) | Exp. Log P/ Hydrophobicity | Predicted Log S | Water Solubility |
|---|---|---|---|---|---|---|
| Ascorbic Acid | 0.0 | 176 | 191 | −0.5 | 0.16 | 40 g/L |
| Aspirin | 0.0 | 180 | 135 | 1.4 | −2.09 | 4.6 mg/mL |
| Colchicine | 0.1 | 399 | 156 | 1.3 | −4.16 | 45 mg/mL |
| Lidocaine | 2.5 | 234 | 68.5 | 2.1 | −2.60 | 4,100 mg/mL |
| Nepafenac | 5.9 | 254 | 184-185 | 2.11* | −3.81 | 0.014* mg/mL |
| Ketorolac | 0.3 | 255 | 165-167 | 2.1 | −2.70 | 25 mg/mL |
| Bromfenac | N/A | 334 | N/A | 3.4 | −4.42 | 0.0126 mg/mL |

As indicated in the above table, higher therapeutic agent Log P values (i.e., indicating greater lipophilicity or hydrophobicity), show a desired therapeutic agent release from the lenses.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

We claim:

1. An ophthalmic device, comprising;
  a mass of material, the mass of material being an acrylic material, the mass of material including at least 70% by weight hydrophobic acrylate and the hydrophobic acrylate being formed of at least 90% by weight of one or more monomers selected from the group consisting of 2-phenyl ethyl acrylate (PEA) and 2-phenyl ethyl methacrylate (PEMA); and
  therapeutic agent disposed upon a peripheral surface of the mass of material wherein the therapeutic agent is hydrophobic and has a PC Log P that is at least 1.6 and wherein the therapeutic agent is an anti-infective agent;
  wherein the mass of material is configured for insertion into an eye of a human and wherein attraction of the therapeutic agent to the hydrophobic acrylate controls sustained release of the therapeutic agent such that less than 50% by weight of the therapeutic agent is released from the mass of material in a period that is at least one week when the mass is submerged in basic salt solution and wherein the mass of material, the device and the therapeutic agent are free of any amino acid.

2. An ophthalmic device as in claim 1 wherein the therapeutic agent has a PC Log P that is at least 2.0.

3. An ophthalmic device as in claim 1 wherein the hydrophobic acrylate is entirely 2-phenyl ethyl methacrylate.

4. An ophthalmic device as in claim 1 wherein the acrylic material includes a substantial portion of hydrophilic acrylate.

5. An ophthalmic device as in claim 4 wherein the hydrophilic acrylate includes 2-hydroxyethylmethacrylate.

6. An ophthalmic device as in claim 4 wherein the mass of material releases a controlled amount of therapeutic agent when submerged in basic salt solution and wherein the hydrophobic acrylate and the hydrophilic acrylate are present in the mass of material in amounts such that the controlled amount of therapeutic agent is less than 60% of the total therapeutic agent in a time period that is at least 5 days.

7. An ophthalmic device as in claim 4 wherein the amount of hydrophilic acrylate and hydrophobic acrylate are selected to provide a predetermined release profile for the therapeutic agent.

8. An ophthalmic device as in claim 1 wherein the therapeutic agent is a quinolone or aminoglycoside.

9. An ophthalmic device as in claim 8 wherein the therapeutic agent is ciprofloxacin, moxifloxacin, or gatifloxacin.

10. An ophthalmic device as in claim 1 wherein the mass of material is an intraocular lens selected from an Aphakic intraocular lens, an anterior Phakic intraocular lens and a posterior chamber Phakic intraocular lens.

11. An ophthalmic device as in claim 1 wherein the mass of material is a haptic of an intraocular lens.

12. An ophthalmic device as in claim 1 wherein the mass of material is located at least partially within an eye of an individual.

13. An ophthalmic device as in claim 1 wherein the mass of material is configured as part or the whole of an intraocular lens, a haptic of an intraocular lens or a separate piece that is inserted in the eye with or without an intraocular lens.

14. An ophthalmic device as in claim 1 wherein the mass of material releases a controlled amount of therapeutic agent when submerged in basic salt solution.

15. An ophthalmic device as in claim 14 wherein less than 50% by weight of the therapeutic agent is released from the ophthalmic device in the basic salt solution over a period that is at least one week.

16. An ophthalmic device as in claim 1 wherein the therapeutic agent has a PC Log P that is at least 1.6 and wherein the attraction of the therapeutic agent to the hydrophobic acrylate provides for sustained release of the therapeutic agent such that less than 50% by weight of the therapeutic agent is released from the mass of material in a period that is at least one week.

17. An ophthalmic device as in claim 16 wherein the hydrophobic acrylate is at least 70% by weight of the mass of material.

18. An ophthalmic device consisting essentially of:
a mass of material, the mass of material being formed of components that consist essentially of acrylic material, cross-linking agent, colored dye and UV absorbing material wherein the acrylic material includes at least 70% by weight hydrophobic acrylate and the hydrophobic acrylate being formed of at least 90% by weight of one or more monomers selected from the group consisting of 2-phenyl ethyl acrylate and 2-phenyl ethyl methacrylate; and
therapeutic agent disposed upon a peripheral surface of the mass of material wherein the therapeutic agent is hydrophobic and has a PC Log P that is at least 1.0 and wherein the therapeutic agent consists of an ophthalmic drug that consists of an anti-infective agent;
wherein the mass of material is configured for insertion into an eye of a human and wherein attraction of the therapeutic agent to the hydrophobic acrylate controls sustained release of the therapeutic agent such that less than 80% by weight of the therapeutic agent is released from the mass of material over a period that is at least three days when the mass is submerged in basic salt solution.

19. An ophthalmic device as in claim 18 wherein the therapeutic agent has a PC Log P that is at least 2.0.

20. An ophthalmic device as in claim 18 wherein the hydrophobic acrylate is entirely 2-phenyl ethyl methacrylate.

21. An ophthalmic device as in claim 18 wherein the mass of material is an intraocular lens selected from an Aphakic intraocular lens, an anterior Phakic intraocular lens and a posterior chamber Phakic intraocular lens.

22. An ophthalmic device as in claim 18 wherein the mass of material is a haptic of an intraocular lens.

23. An ophthalmic device as in claim 18 wherein the mass of material is located at least partially within an eye of an individual.

24. An ophthalmic device as in claim 18 wherein the therapeutic agent has a PC Log P that is at least 1.6 and wherein the attraction of the therapeutic agent to the hydrophobic acrylate provides for sustained release of the therapeutic agent such that less than 50% by weight of the therapeutic agent is released from the mass of material in a period that is at least one week.

* * * * *